(12) United States Patent
Hayashida et al.

(10) Patent No.: US 9,340,579 B2
(45) Date of Patent: May 17, 2016

(54) DPP-4 INHIBITOR

(71) Applicant: NIPPI, INCORPORATED, Tokyo (JP)

(72) Inventors: Osamu Hayashida, Tokyo (JP); Masashi Kusubata, Tokyo (JP); Yuji Atsuzawa, Tokyo (JP); Yuki Taga, Tokyo (JP); Youichi Koyama, Tokyo (JP); Shunji Hattori, Tokyo (JP)

(73) Assignee: NIPPI, INCORPORATED, Tokyo (JP)

( * ) Notice: Subject to any disclaimer, the term of this patent is extended or adjusted under 35 U.S.C. 154(b) by 0 days.

(21) Appl. No.: 14/356,023

(22) PCT Filed: Nov. 2, 2012

(86) PCT No.: PCT/JP2012/078511
§ 371 (c)(1),
(2) Date: May 2, 2014

(87) PCT Pub. No.: WO2013/065832
PCT Pub. Date: May 10, 2013

(65) Prior Publication Data
US 2014/0309401 A1 Oct. 16, 2014

(30) Foreign Application Priority Data
Nov. 4, 2011 (JP) ................................. 2011-242050

(51) Int. Cl.
| | | |
|---|---|---|
| C07K 7/06 | (2006.01) |
| C07K 5/10 | (2006.01) |
| C07K 5/06 | (2006.01) |
| C07K 5/08 | (2006.01) |
| C07K 5/062 | (2006.01) |
| C07K 5/083 | (2006.01) |
| C07K 5/103 | (2006.01) |
| C07K 5/065 | (2006.01) |
| C07K 5/078 | (2006.01) |
| C07K 5/097 | (2006.01) |
| C07K 14/81 | (2006.01) |
| C12N 9/48 | (2006.01) |
| C07K 14/78 | (2006.01) |
| A61K 38/00 | (2006.01) |

(52) U.S. Cl.
CPC ... *C07K 7/06* (2013.01); *C07K 5/06* (2013.01); *C07K 5/06026* (2013.01); *C07K 5/06043* (2013.01); *C07K 5/06078* (2013.01); *C07K 5/06165* (2013.01); *C07K 5/08* (2013.01); *C07K 5/0806* (2013.01); *C07K 5/0808* (2013.01); *C07K 5/0823* (2013.01); *C07K 5/10* (2013.01); *C07K 5/1008* (2013.01); *C07K 14/78* (2013.01); *C07K 14/8103* (2013.01); *C12N 9/485* (2013.01); *C12Y 304/14005* (2013.01); *A61K 38/00* (2013.01)

(58) Field of Classification Search
None
See application file for complete search history.

(56) References Cited

U.S. PATENT DOCUMENTS

| | | |
|---|---|---|
| 2009/0036351 A1 | 2/2009 | Boots |
| 2010/0323377 A1 | 12/2010 | Karsdal et al. |
| 2013/0303448 A1 | 11/2013 | Sugihara et al. |

FOREIGN PATENT DOCUMENTS

| | | |
|---|---|---|
| GB | 2373724 A * | 2/2002 |
| GB | 2 373 724 A | 10/2002 |
| JP | 2007-039424 A | 2/2007 |
| JP | 2009-517464 A | 4/2009 |
| JP | 2010-013423 A | 1/2010 |
| JP | 2011-182742 A | 9/2011 |
| JP | 2011-201923 A | 10/2011 |
| WO | WO 2008/066070 A1 | 6/2008 |
| WO | WO 2012/102308 A1 | 8/2012 |

OTHER PUBLICATIONS

Segal (Polymers of Tripeptides as Collagen Models VII. Synthesis and Solution Properties of Four Collagen-like Polyhexapeptides: J. Mol. Biol. (1969) 43, 497-517).*
Abstract of Jiang et al., "Inhibition of human immunodeficiency virus type 1 infection in a T-cell line (CEM) by new dipeptidyl-peptidase IV (CD26) inhibitors", Res Virol, Jul.-Aug. 1997, vol. 148, No. 4.
Abstract of Reinhold et al., "Role of dipeptidyl peptidase IV (DP IV)-like enzymes in T lymphocyte activation: investigations in DP IV/CD26-knockout mice", Clin Chem Lab Med. 2009, vol. 47, No. 3.
Abstract of Thielitz et al., "The ectopeptidases dipeptidyl peptidase IV (DP IV) and aminopeptidase N (APN) and their related enzymes as possible targets in the treatment of skin diseases", Front Biosci., Jan. 1, 2008, vol. 13.
International Search Report issued in PCT/JP2012/078511, mailed on Jan. 15, 2013.
Ota et al., "DPPIV Sogai Proline Gan'yu Peptide no Kensaku Oyobi Gosei no Kento", The Japanese Society for Food Science and Technology Dai 57 Kai Taikai Koenshu, Sep. 1, 2010, 2Ea6, p. 74.
Written Opinion issued in PCT/JP2012/078511, mailed on Jan. 15, 2013.
Chinese Office Action and English translation dated May 29, 2015 for CN Application No. 201280054376.X.
Chinese Office Action and Search Report for Chinese Application No. 201280054376.X, dated Nov. 20, 2015, with an English translation.

* cited by examiner

*Primary Examiner* — James H Alstrum Acevedo
*Assistant Examiner* — Tara Martinez
(74) *Attorney, Agent, or Firm* — Birch, Stewart, Kolasch & Birch, LLP

(57) ABSTRACT

A DPP-4 inhibitor comprising a peptide represented by the formula (1): Xe-Pro/Ala/Hyp-Xa-Xb-Xc-Xd (SEQ ID NO: 16) (wherein Xe is an amino acid residue with an isoelectric point of 5.9 to 6.3; Pro/Ala/Hyp represents Pro, Ala, or Hyp; Xa is an amino acid residue other than Hyp, Pro, and Arg, or deletion; 5 Xb is Gly, Pro, or deletion; Xc is Pro, Ala, or deletion; and Xd is an amino acid residue or deletion) as an active component. The inhibitor can be expected to bring out an effect of lowering blood glucose levels by enhancing effects of incretins; and the inhibitor may be used as a therapeutic agent for diabetes and, in addition, can act on the immune system or the like to be thus used in 10 treatment for skin diseases or the like.

13 Claims, 2 Drawing Sheets

Fig.3

| AMINO ACID | 3-LETTER ABBREVIATION | MOLECULAR WEIGHT | ISOELECTRIC POINT (pH) |
|---|---|---|---|
| ALANINE | Ala | 89.09 | 6.00 |
| ARGININE | Arg | 174.20 | 10.76 |
| ASPARAGINE | Asn | 132.12 | 5.41 |
| ASPARTIC ACID | Asp | 133.10 | 2.77 |
| CYSTEINE | Cys | 121.16 | 5.05 |
| GLUTAMINE | Gln | 146.15 | 5.65 |
| GLUTAMIC ACID | Glu | 147.13 | 3.22 |
| GLYCINE | Gly | 75.07 | 5.97 |
| HISTIDINE | His | 155.15 | 7.59 |
| HYDROXYPROLINE | Hyp | 131.13 | 5.74 |
| ISOLEUCINE | Ile | 131.17 | 6.05 |
| LEUCINE | Leu | 131.17 | 5.98 |
| LYSINE | Lys | 146.19 | 9.75 |
| METHIONINE | Met | 149.21 | 5.74 |
| PHENYL ALANINE | Phe | 165.19 | 5.48 |
| PROLINE | Pro | 115.13 | 6.30 |
| SERINE | Ser | 105.09 | 5.68 |
| THREONINE | Thr | 119.12 | 6.16 |
| TRYPTOPHAN | Trp | 204.23 | 5.89 |
| TYROSINE | Tyr | 181.19 | 5.66 |
| VALINE | Val | 117.15 | 5.96 |

DPP-4 INHIBITOR

REFERENCE TO SEQUENCE LISTING SUBMITTED VIA EFS-WEB

This application includes a sequence listing in .txt form electronically submitted via EFS-Web. The .txt file contains a sequence listing entitled "2015-07-21 6175-0106PUS1_ST25.txt" created on Jul. 21, 2015 and is 20,012 bytes in size. The sequence listing contained in this .txt file is part of the specification and is hereby incorporated by reference herein in its entirety.

TECHNICAL FIELD

The present disclosure relates to a dipeptidyl peptidase-4 inhibitor (hereinafter referred to simply as a DPP-4 inhibitor) comprising a peptide with 2 to 6 amino acids that has a specific sequence.

BACKGROUND ART

Diabetes mellitus is a chronic disease that causes systemic metabolic disorders such as hyperglycemia, glycosuria, disintegration of body proteins, ketosis, or acidosis. In general, diabetes is roughly divided into type 1 and type 2 diabetes, wherein β cells in the pancreas are for some reason disrupted to deplete insulin which regulates blood glucose levels in the type 1; whereas insulin is present in the blood but does not function properly or the amount of insulin secreted from pancreatic β cells decreases, resulting in impaired regulation of blood glucose level in the type 2.

Recently, as a hormone that regulates the blood glucose level, incretins which are one of the gastrointestinal hormones have drawn much attention. The incretin is a collective term for hormones that are secreted from the gastrointestinal tract in association with food ingestion and that acts on pancreatic β cells to promote insulin secretion. There are two known incretins, namely glucose-dependent insulinotropic polypeptide (GIP) and glucagon-like peptide-1 (GLP-1). The secreted incretin binds to its receptor on the surface of pancreas β cells to promote the insulin secretion and suppress glucagon secretion, thereby exhibiting an effect of lowering the blood glucose level. The effect of promoting the insulin secretion by incretins depends on glucose concentration in the blood and is brought out only when glucose is present at a certain concentration or higher. That is, there is a less risk of occurrence of hypoglycemia which is a concern in direct insulin administration which is a conventional treatment method; and after-meal hyperglycemia can be expected to be safely corrected. As a matter of fact, it has been revealed that continuous administration of GLP-1 which is one of the incretins to patients with type 2 diabetes via the veins promotes the insulin secretion and thereby blood glucose control is significantly improved, demonstrating usefulness of GLP-1 supplemental therapy.

Meanwhile, GLP-1 is rapidly degraded by dipeptidyl peptidase-4 (EC3.4.14.5, hereinafter referred to simply as DPP-4) which is extensively present in the living body. In view of this, as a method of treating diabetes, new drug agents have been developed, which new drug agents inhibit the activity of DPP-4 to keep and enhance an effect of endogenous GLP-1. It is to be noted that DPP-4 is a serine protease that is expressed on the plasma membrane as CD26 of immune cells such as T cells and is also present as a soluble protein in the blood to inactivate GLP-1. DPP-4 specifically acts on a biologically active peptide with Pro or Ala at the second position from the N-terminal to allow dipeptide to be freed from the N-terminal.

On the basis of such an effect of DPP-4, a DPP-4 inhibitor comprising a peptide having 3 to 12 amino acids is available, wherein Pro is arranged at the second position from the N-terminal (Patent Literature 1). The DPP-4 inhibitor is a peptide that is contained in a water-soluble fraction obtained by suspending cheese in an aqueous solvent and then removing insoluble substances; and when orally taken, a food or drink in which such a peptide is contained can lower blood glucose levels in the living body. The DPP-4 inhibitor described in Patent Literature 1 is obtained from a natural product and is thus said to be low in toxicity and high in safety.

Further, also available is a peptide that is a milk protein hydrolysate, stimulates GLP-1 secretion, and has a DPP-4 inhibitory effect (Patent Literature 2). It is described that the peptide disclosed in Patent Literature 2 is preferably one with 2 to 8 amino acids in length that contains Pro as the second N-terminal residue. In the examples, as a certain milk protein hydrolysate, a peptide composition of 500 to 2000 Da was evaluated for the DPP-4 inhibitory effect thereof, yet the composition and peptide sequence thereof are unknown.

Further, also available is a DPP-4 inhibitor that contains a preparation derived from a material for eating or drinking as an active component (Patent Literature 3). It is one that contains, as an active component, a preparation derived from a material for eating and drinking, the preparation exhibiting a DPP-4 inhibition rate of 60% or more at a solid concentration of 3.5 mg/ml or less. In the examples in Patent Literature 3, peptides derived from mung beans, soybeans, collagen, seaweed, green tea, walnuts, tian cha, pomegranate, grape seeds, and the like are evaluated for the DPP-4 inhibition rate thereof.

Further, also available as a DPP-4 inhibitor is a peptide derived from collagen or gelatin, which peptide is represented by Gly-X-Y-(Gly-Z-W)n (SEQ ID NO: 15) (wherein n is an integer of 0 to 4; X is Pro or Leu; Y, Z, and W are the same or different and represent each independently any amino acid residue (with the proviso that Gly is excluded) (Patent Literature 4). In the examples, a commercially available collagen peptide is fractionated by high performance liquid chromatography and the sequence of peptide in a fraction that has an excellent DPP-4 inhibitory activity is specified.

Meanwhile, as an effect of a DPP-4 inhibitor, suppression of T lymphocyte proliferation has been known (Non Patent Literature 1). Non Patent Literature 1 points out that the DPP-4 inhibitor can alleviate autoimmune diseases such as autoimmune spondylitis, multiple sclerosis, arthritis, or rheumatism. In addition, because DPP-4 is involved in acceleration of HIV-1 infection through CD4 positive T cells, it has also been reported that use of a DPP-4 inhibitor in combination with other drug agents is expected to protect against HIV-1 infection (Non Patent Literature 2). Further, because DPP-4 is expressed by skin cells, it has also been reported that a DPP-4 inhibitor may have an influence on proliferation, differentiation, or cytokine production of sebaceous gland cells or epidermal cells (Non Patent Literature 3). It is implicated that T lymphocyte proliferation stimulated by acne bacteria is suppressed by the DPP-4 inhibitor, which causes suppression of fibroblasts' TGF-β expression, suppression of fibroblast proliferation, suppression of fibroblasts' matrix production; and, as a result, acne, psoriasis, and keloid can be treated by the DPP-4 inhibitor.

CITATION LIST

Patent Literature

Patent Literature 1: Unexamined Japanese Patent Application Kokai Publication No. 2007-39424
Patent Literature 2: National Patent Publication No. 2009-517464
Patent Literature 3: Unexamined Japanese Patent Application Kokai Publication No. 2010-13423
Patent Literature 4: International Publication No. WO 2008/066070

Non Patent Literature

Non Patent Literature 1: Role of dipeptidyl peptidase IV (DP IV)-like enzymes in T lymphocyte activation: investigations in DP IV/CD26-knockout mice, Clin Chem Lab Med. 2009; 47(3):268-74.
Non Patent Literature 2: Inhibition of human immunodeficiency virus type 1 infection in a T-cell line (CEM) by new dipeptidyl-peptidase IV (CD26) inhibitors. Res Virol. 1997 July-August; 148(4):255-66.
Non Patent Literature 3: The ectopeptidases dipeptidyl peptidase IV (DP IV) and aminopeptidase N (APN) and their related enzymes as possible targets in the treatment of skin diseases. Front Biosci. 2008 Jan. 1; 13:2364-75.

SUMMARY OF INVENTION

Technical Problem

The above DPP-4 inhibitors described in Patent Literatures 1 to 4 are excellent in safety in that all utilize natural products such as cheese, milk proteins, or other materials for eating or drinking as a raw material; yet development of a DPP-4 inhibitor having a stronger inhibitory effect is desired.

That is, Patent Literature 1 and Patent Literature 2 are limited to a specific peptide sequence and the DPP-4 inhibitory effect related to other sequences is unknown. Further, these peptides described in Patent Literature 1 are, in the first place, limited to ones derived from a water-soluble fraction of cheese and thus the DPP-4 inhibitory effect related to other sequences are also unknown. Further, Patent Literature 2 selects, as a preferred peptide, one with 2 to 8 amino acids in length that contains Pro as the first, second, third, or fourth residue from the N-terminal; or that contains Pro as the C-terminal residue or the second position from the C-terminal. These focus attention on a fact that DPP-4 acts on biologically-active peptides that specifically have Pro or Ala at the second position from the N-terminal. However, as for hydrolysates evaluated for the DPP-4 inhibitory effect thereof in the examples, a relationship between molecular weight distribution and DPP-4 inhibition, and GLP-1 secretion is evaluated, yet the composition of hydrolysates used is unknown.

Patent Literature 3 evaluates the DPP-4 inhibition rate of porcine and piscine collagen peptides, yet there is no mention of a specific peptide sequence. Further, incretins are rapidly degraded as substrates of DPP-4 and thus the half life thereof in the blood is very short. Therefore, in order to secure incretin concentration in the blood by a DPP-4 inhibitor, a DPP-4 inhibitory effect has to be rapidly brought out in the blood and the DPP-4 inhibitor has to exhibit excellent absorption into the living body.

Meanwhile, a peptide used in the examples in Patent Literature 4 is one obtained by fractionating a commercially available collagen peptide by a reversed phase column and isolating a peptide that has an excellent DPP-4 inhibitory activity. The peptide sequence and DPP-4 inhibitory activity thereof are not systematically evaluated. In addition, collagen which is a raw material is, in the first place, a commercially available gelatin that has been subjected to collagenase treatment. Because peptides with Gly at the N-terminal are major components in the degradation by collagenase, peptides with an amino acid residue other than Gly at the N-terminal or peptides with Gly at the C-terminal cannot be produced to evaluate the DPP-4 inhibitory activity.

Meanwhile, as shown in Non Patent Literature 1 to Non Patent Literature 3, the DPP-4 inhibitor can act on the immune system and can be used in medical applications including treatment of skin diseases, and therefore there is the possibility of expanding the application thereof.

Under these circumstances, development of a DPP-4 inhibitor derived from a peptide that is high in safety is desired.

Solution to Problem

In order to solve the above object, the present inventors synthesized various peptides while referring to the amino acid primary structure of collagen, and evaluate a DPP-4 inhibitor. As a result, they found out that even when the second amino acid residue from the N-terminal is Hyp, a DPP-4 inhibitory activity can be brought out; even when the second residue from the N-terminal is Pro or Ala, peptides with no DPP-4 inhibitory activity exists; when the third amino acid residue from the N-terminal is Gly, an excellent DPP-4 inhibitory activity is brought out, thereby completing the present disclosure. On top of that, because the peptide used in the present disclosure is a peptide with a specific sequence comprising 2 to 6 amino acids, it exhibits excellent mobility into the blood and is able to rapidly bring out the DPP-4 inhibitory effect thereof; and because it has a amino acid sequence derived from collagen it is excellent in safety.

That is, the present disclosure provides a DPP-4 inhibitor comprising a peptide represented by the formula (1): Xe-Pro/Ala/Hyp-Xa-Xb-Xc-Xd (SEQ ID NO: 16) (wherein Xe is an amino acid residue with an isoelectric point of 5.9 to 6.3; Pro/Ala/Hyp represents Pro, Ala, or Hyp; Xa is an amino acid residue other than Hyp, Pro, and Arg, or deletion; Xb is Gly, Pro, or deletion; Xc is Pro, Ala, or deletion; and Xd is an amino acid residue or deletion) as an active component.

Further, the present disclosure provides the above DPP-4 inhibitor, wherein the above-mentioned peptide is either the formula (A): Gly-Pro/Ala-Xa-Xb-Xc-Xd (SEQ ID NO: 17) (wherein Pro/Ala represents Pro or Ala; Xa is an amino acid residue other than Hyp, Pro, and Arg, or deletion; Xh is Gly or deletion; Xc is Pro or deletion; and Xd is an amino acid residue or deletion), or the formula (B): Leu/Ile/Ala-Hyp/Pro-Xa-Xb-Xc (SEQ ID NO: 18) (wherein Leu/Ile/Ala represents Leu, Ile, or Ala; Hyp/Pro represents Hyp or Pro; Xa is an amino acid residue other than Hyp, Pro, Ile, and Arg, or deletion; Xb is Pro or deletion; and Xc is Ala or deletion).

Further, the present disclosure provides the above DPP-4 inhibitor, wherein the above-mentioned peptide is any of the formula (A-1): Gly-Pro-Xa-Xb-Xc-Xd (SEQ ID NO: 19) (wherein Xa is an amino acid residue with an isoelectric point of 3.0 to 6.2 other than Hyp; Xb is Gly or deletion; Xc is Pro or deletion; and Xd is an amino acid residue or deletion); the formula (A-2): Gly-Ala-Xa-Xb-Xc-Xd (SEQ ID NO: 20) (wherein Xa is an amino acid residue with an isoelectric point of 5.8 to 6.2 or deletion; Xb is Gly or deletion; Xc is Pro or deletion; and Xd is an amino acid residue or deletion); the formula (B-1): Leu-Pro-Xa-Xb-Xc (SEQ ID NO: 22) (wherein Xa is Gly or deletion; Xb is Pro or deletion; and Xc is Ala or deletion); the formula (B-2): Leu/Ile-Hyp-Xa-Xb-Xc (SEQ ID NO: 21) (wherein Leu/Ile represents Leu or Ile; Xa is Gly or deletion; Xb is Pro or deletion; and Xc is Ala or deletion); or the formula (B-3): Ala-Hyp/Pro-Gly (wherein Hyp/Pro represents Hyp or Pro).

In addition, the present disclosure provides the above DPP-4 inhibitor, wherein the above-mentioned peptide is any one or more types selected from the group consisting of Gly-Pro-Ala-Gly (SEQ ID NO: 1), Gly-Pro-Ala-Gly-Pro (SEQ ID NO: 2), Gly-Pro-Ala-Gly-Pro-Arg (SEQ ID NO: 3), Gly-Pro-Ala-Gly-Pro-Hyp (SEQ ID NO: 4), Gly-Pro-Ala-Gly-Pro-Ile (SEQ ID NO: 5), Gly-Pro-Leu-Gly-Pro-Val (SEQ ID NO: 6), Gly-Pro-Ile-Gly-Pro-Val (SEQ ID NO: 7), Gly-Pro-Val, Gly-Pro-Gln, Gly-Pro-Glu, Gly-Ala, Gly-Ala-Ile-Gly-Pro-Ala (SEQ ID NO: 8), Gly-Ala-Ile-Gly-Pro-Ser (SEQ ID NO: 9), Gly-Ala-Val-Gly-Pro-Ala (SEQ ID NO: 10), Gly-Ala-Val-Gly-Pro (SEQ ID NO: 11), Leu-Pro, Leu-Pro-Gly, Leu-Pro-Gly-Pro-Ala (SEQ ID NO: 12), Ala-Pro-Gly, Ile-Hyp-Gly, and Leu-Hyp-Gly-Pro-Ala (SEQ ID NO: 13).

Further, the present disclosure provides the above DPP-4 inhibitor, wherein the above-mentioned peptide is a mixture of any one or more types of the formula (A): Gly-Pro/Ala-Xa-Xb-Xc-Xd (SEQ ID NO: 17) (wherein Pro/Ala represents Pro or Ala; Xa is an amino acid residue other than Hyp, Pro, and Arg, or deletion; Xb is Gly or deletion; Xc is Pro or deletion; and Xd is an amino acid residue or deletion) with any one or more types of the formula (B): Leu/Ile/Ala-Hyp/Pro-Xa-Xb-Xc (SEQ ID NO: 18) (wherein Leu/Ile/Ala represents Leu, Ile, or Ala; Hyp/Pro represents Hyp or Pro; Xa is an amino acid residue other than Hyp, Pro, Ile, and Arg, or deletion; Xb is Pro or deletion; and Xc is Ala or deletion).

Advantageous Effects of Invention

According to the present disclosure, provided is a novel DPP-4 inhibitor that is excellent in safety as well as has an excellent DPP-4 inhibitory activity.

BRIEF DESCRIPTION OF DRAWINGS

FIG. 3 is a list showing the isoelectric point of amino acids.

DESCRIPTION OF EMBODIMENTS

Figure 1:
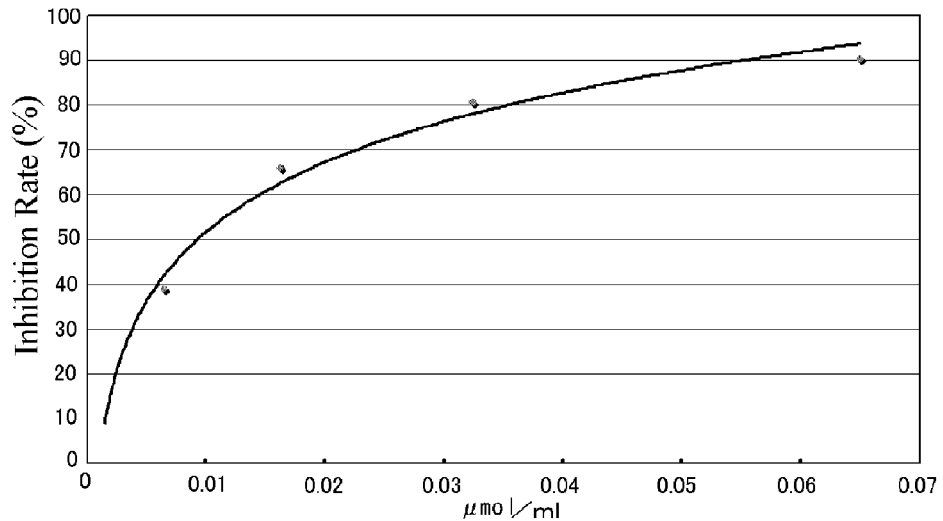
FIG. 1 is a figure showing the DPP-4 inhibition curve of the peptide synthesized in Example 6 (Gly-Pro-Ile-Gly-Pro-Val); (SEQ ID NO: 7)

A first of the present disclosure is a DPP-4 inhibitor including a peptide represented by the formula (1): Xe-Pro/Ala/H-Xa-Xb-Xc-Xd (SEQ ID NO: 16) (wherein Xe is an amino acid residue with an isoelectric point of 5.9 to 6.3; Pro/Ala/Hyp represents Pro, Ala, or Hyp; Xa is an amino acid residue other than Hyp, Pro, and Arg, or deletion; Xb is Gly, Pro, or deletion; Xc is Pro, Ala, or deletion; and Xd is an amino acid residue or deletion) as an active component.

Human DPP-4 is a membrane protein of 110 kDa comprising 766 amino acids; and is an enzyme in which a β propeller domain is arranged at the amino-group-side terminal and an α/β hydrolase domain is arranged at the carboxyl-group-side terminal, wherein three catalyst residues (Ser630, His740, and Asp708) are present in the above-mentioned α/β hydrolase domain. In the blood, the extracellular domain is cleaved from the membrane binding region to be present as a soluble form. In light of the specificity of allowing dipeptides to freed from peptides having Pro or Ala at the second position from the N-terminal, as shown in, for example, the above-mentioned Patent Literature 1, various peptides in which Ala or Pro is arranged at the second position from the amino terminal are proposed as DPP-4 inhibitors and the $IC_{50}$ thereof are measured. Further, it has been known that Diprotin A (Ile-Pro-Ile), in spite of being a substrate of DPP-4, acts like an inhibitor because both the $k_{cat}$ and $K_m$ value thereof are low; and the $IC_{50}$ measurement value of Diprotin A in conjunction with various peptides are described also in the examples in Patent Literature 1.

In order to develop peptides that were excellent in safety and that had an excellent DPP-4 inhibitory effect under these circumstances, various peptides were synthesized, referring to the amino acid sequence of collagen as a peptide containing a large number of Pro residues.

It is to be noted that collagen is a protein that has the triple helical structure of three polypeptide chains as a base unit and that composes the dermis, ligament, tendon, bone, cartilage, or the like of the living body. A collagen fiber is formed by association of plural collagen molecules. Amino acids that compose collagen molecules have the primary structure that is referred to as a so-called "collagen-like sequence" in which Gly repeats every three residues, which collagen-like sequence is represented by -Gly-amino acid X-amino acid Y-. Examples of amino acids specific to collagen include hydroxyproline (Hyp) and hydroxylysine (Hyl) in which one hydroxyl group is attached to Pro and Lys. In many of the above-mentioned collagen-like sequence, Pro is present as the above-mentioned amino acid X, or Hyp is present as the amino acid Y; and the triple helical structure is maintained by this collagen-like sequence. When processed, collagen which is tough is subjected to hydrolysis by an acid, alkali, or enzyme to be processed into gelatin or others. As such an enzyme, there is collagenase; and it is commonly used. Collagenase is an endopeptidase that mainly generates peptides with Gly at the N-terminal. Therefore, conventional collagen degradation products have peptides with Gly at the N-terminal as a major component. In view of this, for the purpose of creating peptides that were not restricted by such an enzymatic hydrolysis and had an excellent DPP-4 inhibitory activity, various peptides are synthesized by referring the amino acid sequence of collagen to pick out a part thereof or alter a part of the sequence picked out and the inhibition rate thereof for DPP-4 was evaluated in the present disclosure.

Because the peptide evaluated in the disclosure of the present application is one obtained by referring the amino acid sequence of collagen, collagen is, metabolized in accordance with a usual process when ingested in the living body and is high in safety. For reference, the bovine-derived type I collagen α1 chain is set forth in SEQ ID NO: 14. This sequence is registered under NCBI accession number NP 001029211. It is to be noted that Hyp contained in collagen is one obtained by modifying Pro by proline hydroxylase after collagen is generated. SEQ ID NO: 14 is an amino acid sequence prior to posttranslational modification and does not include Hyp. The present disclosure will now be described in detail below.

The DPP-4 inhibitor of the present disclosure has a peptide represented by the formula (1): Xe-Pro/Ala/Hyp-Xa-Xb-Xc-Xd (SEQ ID NO: 16) (wherein Xe is an amino acid residue with an isoelectric point of 5.9 to 6.3; Pro/Ala/Hyp represents Pro, Ala, or Hyp; Xa is an amino acid residue other than Hyp, Pro, and Arg, or deletion; Xb is Gly, Pro, or deletion; Xc is Pro, Ala, or deletion; and Xd is an amino acid residue or deletion) as an active component. When the amino acid sequence and DPP-4 inhibitory activity are closely examined, it was found that in cases where the third amino acid residue from the N-terminal is Hyp or Pro, regardless of other amino acid residues the DPP-4 inhibitory activity is low or no DPP-4 inhibitory activity is borne. Further, in cases where the second amino acid residue from the N-terminal is Pro, Ala, or Hyp, the DPP-4 inhibitory activity is excellent; and if the above condition is satisfied, the amino acid residue of the N-terminal may be widely selected in a range of an isoelectric point of 5.9 to 6.3. As Xe, preferred is Gly, Ala, Ile, Leu, or Pro; and more preferred is Gly, Ala, Ile, or Leu.

The peptide represented by the above the formula (1) may also be the formula (A): Gly-Pro/Ala-Xa-Xb-Xc-Xd (SEQ ID NO: 17) (wherein Pro/Ala represents Pro or Ala; Xa is an amino acid residue other than Hyp, Pro, and Arg, or deletion; Xb is Gly or deletion; Xc is Pro or deletion; and Xd is an amino acid residue or deletion).

In cases where the N-terminal is Gly, Xa is preferably an amino acid residue other than Hyp, Pro, and Arg. Because DPP-4 has the specificity of allowing dipeptides to be freed from peptides having Pro or Ala at the second position from the N-terminal, it is speculated that peptides with Pro or Ala at the second amino acid residue from the N-terminal have the DPP-4 inhibitory activity. However, even when the second amino acid residue was Pro or Ala, it was found that, when the third amino acid residue from the N-terminal was Hyp or Pro, the DPP-4 inhibitory activity was extremely low or was not present at all.

Further, in cases where the second amino acid residue from the N-terminal is Pro, Xa is preferably an amino acid residue having an isoelectric point of pH 3.0 to 6.2 other than Hyp, such as Ala, Gln, Glu, Ile, Leu, or Val. It is in particular preferred to be Ala, Gln, Glu, Ile, Leu, or Val.

Meanwhile, in cases where the second amino acid residue from the N-terminal is Ala, Xa is an amino acid residue having an isoelectric point of pH 5.8 to 6.2 such as Val, Leu, or Ile, or deletion. That's because, as shown in the examples described later, regardless of the amino acid sequence in the fourth and farther positions from the N-terminal, the DPP-4 inhibitory activity is excellent. Note that, in the present disclosure, the isoelectric point of amino acid complied with the numerical value shown in FIG. 3.

In the above the formula (A), Xb is Gly or deletion; and when Xb is deletion, the obtained peptide is a tripeptide.

Xc is Pro or deletion and when Xc is deletion, the obtained peptide is a tetrapeptide. Further, Xd may be any amino acid residue or may be deletion. The peptide represented by the above-mentioned general formula (A), the peptide used in the present disclosure has the sequence of Gly-Pro/Ala- from the N-terminal; and exhibits, as shown in the examples described later, a tendency that the DPP-4 inhibitory activity increases as the peptide chain becomes longer in a range where the number of amino acids is 2 to 6 whereas the rate of increasing the activity levels off when the number of amino acid residues is above 5. This means that the DPP-4 inhibitory activity is determined by the sequence from the N-terminal residue to the fourth residue therefrom whereas the sixth amino acid residue from the N-terminal can be any type of amino acid residue. When different amino acid residues was linked as Xd and the DPP-4 inhibitory activity was evaluated, the DPP-4 inhibitory activity is brought out in peptides with a wide range of amino acid residues being linked, which acid residues include Arg which is hydrophilic and has an isoelectric point of above pH 10; Hyp which is one type of imino acids; Ile, Val, Ser, and Ala which are hydrophobic and whose isoelectric point is in the weak acid side.

The peptide represented by the formula (A), the peptide used in the present disclosure may also be the formula (A-1): Gly-Pro-Xa-Xb-Xc-Xd (SEQ ID NO: 19) (wherein Xa is an amino acid residue with an isoelectric point of 3.0 to 6.2 other than Hyp; Xb is Gly or deletion; Xc is Pro or deletion; and Xd is an amino acid residue or deletion).

Xa shown in the above formula (A-1) is preferably Ala, Gln, Glu, Ile, Val, or Leu; and Xd is preferably Ala, Hyp, Leu, Val, Arg, or deletion.

Further, the peptide represented by the formula (A), the peptide used in the present disclosure may also be the formula (A-2): Gly-Ala-Xa-Xb-Xc-Xd (SEQ ID NO: 20) (wherein Xa is an amino acid residue with an isoelectric point of 5.8 to 6.2 or deletion; Xb is Gly or deletion; Xc is Pro or deletion; and Xd is an amino acid residue or deletion).

Xa shown in the above formula (A-2) is preferably Leu, Ile, Val, or deletion; and Xd is preferably Ala, Ser, or deletion.

In the DPP-4 inhibitor of the present disclosure, the peptides represented by the above the formula (A) include Gly-Pro-Ala-Gly (SEQ ID NO: 1), Gly-Pro-Ala-Gly-Pro (SEQ ID NO: 2), Gly-Pro-Ala-Gly-Pro-Arg (SEQ ID NO: 3), Gly-Pro-Ala-Gly-Pro-Hyp (SEQ ID NO: 4), Gly-Pro-Ala-Gly-Pro-Ile (SEQ ID NO: 5), Gly-Pro-Leu-Gly-Pro-Val (SEQ ID NO: 6), Gly-Pro-Ile-Gly-Pro-Val (SEQ ID NO: 7), Gly-Pro-Val, Gly-Pro-Gln, Gly-Pro-Glu, Gly-Ala, Gly-Ala-Ile-Gly-Pro-Ala (SEQ ID NO: 8), Gly-Ala-Ile-Gly-Pro-Ser (SEQ ID NO: 9), Gly-Ala-Val-Gly-Pro-Ala (SEQ ID NO: 10), and Gly-Ala-Val-Gly-Pro (SEQ ID NO: 11).

Further, the DPP-4 inhibitor of the present disclosure may also be a peptide represented by the formula (B): Leu/Ile/Ala-Hyp/Pro-Xa-Xb-Xc (SEQ ID NO: 18) (wherein Leu/Ile/Ala represents Leu, Ile, or Ala; Hyp/Pro represents Hyp or Pro; Xa is an amino acid residue other than Hyp, Pro, Ile, and Arg, or deletion; Xb is Pro or deletion; and Xc is Ala or deletion).

Although collagen contained the collagen-like sequence represented by -Gly-amino acid X-amino acid Y-, when the DPP-4 inhibitory activity was evaluated without limiting the N-terminal to Gly, it was found that the DPP-4 inhibitory activity was excellent when the third amino acid residue from the N-terminal is Gly. In this occasion, the amino acid residue at the N-terminal was Leu, Ile, or Ala; and there was a tendency that the DPP-4 inhibitory activity increased as the length of the peptide became longer. The second amino acid from the N-terminal may be Pro or Hyp. Although DPP-4 has the specificity of allowing dipeptides to be freed from peptides having Pro or Ala at the second position from the N-terminal, in cases where the N-terminal is Phe, Pro, or Ala, even when the second amino acid from the N-terminal is Pro or Hyp, the DPP-4 inhibitory activity is low or is not present at all. This means that the DPP-4 inhibitory activity is affected by the type of the amino acid residue at the N-terminal as well. Yet, also in this occasion, when Gly is linked as the third amino acid residue from the N-terminal, the DPP-4 inhibitory activity increased. When Xa is deletion, the obtained peptide is a dipeptide; and when Xb is deletion, the obtained peptide is a tripeptide. It is to be noted that, when the amino acid sequence of collagen is referred, it cannot be assumed that the amino acid residue of Xa is Ile in the formula (B) and thus Xa is regarded to be an amino acid residue other than Hyp, Pro, Ile, and Arg or to be deletion.

As the peptide represented by the formula (B), the peptide used in the present disclosure, the formula (B-1): Leu-Pro- Xa-Xb-Xc (SEQ ID NO: 22) (wherein Xa is Gly or deletion; Xb is Pro or deletion; and Xc is Ala or deletion) can preferably be used.

Further, the peptide represented by the formula (B), the peptide used in the present disclosure may also be the formula (B-2): Leu/Ile-Hyp-Xa-Xb-Xc (SEQ ID NO: 21) (wherein Leu/Ile represents Leu or Ile; Xa is Gly or deletion; Xb is Pro or deletion; and Xc is Ala or deletion).

Further, the peptide represented by the formula (B), the peptide used in the present disclosure may also be the formula (B-3): Ala-Hyp/Pro-Gly (wherein Hyp/Pro represents Hyp or Pro).

In the DPP-4 inhibitor of the present disclosure, the peptides represented by the above formula (B) include Leu-Pro, Leu-Pro-Gly, Leu-Pro-Gly-Pro-Ala (SEQ ID NO: 12), Ala-Pro-Gly, Ile-Hyp-Gly, and Leu-Hyp-Gly-Pro-Ala (SEQ ID NO: 13).

The above peptide used in the DPP-4 inhibitor of the present disclosure may be one that composes a medically acceptable salt. It is to be noted that a medically acceptable salt refers to a form of salt that is pharmacologically acceptable and is a compound of the present disclosure that is substantially nontoxic for subjects who are administrated therewith. Examples of the medically acceptable salt of the above peptide include inorganic salts such as sodium salts, calcium salts, magnesium salts, and calcium salts; organic acid salts such as acetate, propionate, glycolate, lactate, hydroxybutyrate, malate, maleate, malonate, succinate, adipate, tartrate, citrate, and glutarate; and addition salts such as hydrochloride, phosphate, sulfate, carboxylate, phosphonate, and sulfonate.

The DPP-4 inhibitor of the present disclosure is, as mentioned above, one with an excellent DPP-4 inhibitory effect that is selected by referring to the amino acid primary sequence of collagen or that is obtained by partially altering the sequence; and can be produced by peptide synthesis. Yet, it may be one that is prepared by other methods.

The DPP-4 inhibitor of the present disclosure can be orally administrated to inhibit DPP-4 in the living body to thereby lower blood glucose levels and can be used as a prophylactic agent or therapeutic agent for diabetes. As for a dosage form of the DPP-4 inhibitor of the present disclosure in the case of oral administration, the peptide may be used as is. Besides it may be combined with other excipients to prepare tablets, fine granules, pills, troches or the like; or may be placed in a capsule to use as encapsulated formulations. Further, it can be prepared into solution or the like. For the case of the oral administration, selection can be made as appropriate in consideration of conditions including an object of treatment or prophylaxis, symptoms, body weight, and age. Further, it can also be taken as a supplement.

The dose of the DPP-4 inhibitor of the present disclosure can be selected as appropriate according to dosage forms, an object of administration, the age of subject, or the like. In general, in the case of oral administration, the dose for adults is 0.001 to 100 mg/kg per day, preferably 0.01 to 50 mg/kg, and more preferably 0.1 to 20 mg/kg. In the case of injections, the dose is, for example, 0.0001 to 50 mg/kg, preferably 0.001 to 20 mg/kg, and in particular preferably 0.01 to 10 mg/kg.

As for such a peptide, a mixture of any one or more types represented by the formula (A): Gly-Pro/Ala-Xa-Xb-Xc-Xd (SEQ ID NO: 17) (wherein Pro/Ala represents Pro or Ala; Xa is an amino acid residue other than Hyp, Pro, and Arg, or deletion; Xb is Gly or deletion; Xc is Pro or deletion; and Xd is an amino acid residue or deletion) with any one or more types represented by the formula (B): Leu/Ile/Ala-Hyp/Pro-Xa-Xb-Xc (SEQ ID NO: 18) (wherein Leu/Ile/Ala represents Leu, Ile, or Ala; Hyp/Pro represents Hyp or Pro; Xa is an amino acid residue other than Hyp, Pro, Ile, and Arg, or deletion; Xb is Pro or deletion; and Xc is Ala or deletion) can be suitably used as a DPP-4 inhibitor. The formula (A) has Gly at the N-terminal whereas the formula (B) has an amino acid residue other than Gly at the N-terminal and thus all of the peptides differ in a metabolic rate after ingestion and the like, albeit derived from the amino acid sequence of collagen. That's why an effect of combined use can be expected.

The DPP-4 inhibitor of the present disclosure can be combined in food products to be orally taken. Examples of such food products in which the DPP-4 inhibitor of the present disclosure is combined include juice and beverages that contain vegetables, fruits, lactobacillus, or the like; and semisolid food products such as jellies, yogurts, puddings, or ice cream. Besides, the DPP-4 inhibitor can be kneaded and mixed in other food materials to prepare into solid food products.

Further, the DPP-4 inhibitor has an effect of proliferating T lymphocytes and, in addition, it has been pointed out that the DPP-4 inhibitor alleviates autoimmune diseases such as autoimmune spondylitis, multiple sclerosis, arthritis, or rheumatism. Therefore, the DPP-4 inhibitor of the present disclosure can also be potentially used for the above diseases. Applications on this occasion are not limited to internal use and may be used as surgical prescription including infusion into inflammatory sites.

EXAMPLES

By way of the examples, the present disclosure will be specifically described below. However, the present disclosure is by no means limited to these examples.

Method of Measuring Inhibitory Activity of DPP-4

(1) Method of Measuring Inhibition Rate of DPP-4

A sample liquid 35 µl obtained by dissolving a sample 1 mg in 50 mM tris-hydrochloric acid buffer (pH 7.5) 1 ml and DPP-4 (manufactured by Sigma, derived from porcine kidney; 8.6 mU/ml) 15 µl that had been dissolved in 50 mM tris-hydrochloric acid buffer (pH 7.5) were mixed in a microtiter plate well (manufactured by NUNC, trade name "237015") and incubated at 37° C. for 10 minutes.

Thereto, 50 µl of a substrate solution (one obtained by dissolving glycyl-Pro-4-methylcoumarin-7-amide (Gly-Pro-MCA) in 50 mM tris-hydrochloric acid buffer (pH 7.5) so as to be 10 µM) that had in advance heated to and kept at 37° C. was added, mixed, and allowed to react at 37° C. for 20 minutes.

The fluorescence intensity of 7-amino-4-methylcoumarin (AMC) that was freed by DPP-4 was measured with time by a microplate reader type fluorescence detector (manufactured by Corona Electric Co., Ltd., trade name "SH-9000"). Note that the measurement wavelength was an excitation wavelength of 380 nm and a measurement wavelength of 460 nm. Note that one obtained by using the same amount of 50 mM tris-hydrochloric acid buffer (pH 7.5) in replace of the sample was used as a control; and the fluorescence intensity thereof was measured.

The activity of DPP-4 was expressed by an average gradient of change in the amount of the fluorescence intensity during the reaction time; and, as for DPP-4 inhibition rate, difference obtained by, with the control as 100%, subtracting the activity of the sample from the above-mentioned control was calculated as an inhibition rate (%).

(2) Method of Measuring $IC_{50}$ Value

In accordance with the above method of measuring a DPP-4 inhibition rate, sample concentration was changed between 0.001 and 7.2 µmol/ml to obtain the inhibition rate, thereby calculating the 50% inhibitory concentration ($IC_{50}$ value) of the activity of DPP-4.

Example 1

Gly-Pro-Ala-Gly-Pro (SEQ ID NO: 2) shown in Table 1 was synthesized by an Fmoc solid phase 18 synthesis method using an automatic peptide synthesizer (433A) manufactured by Applied Biosystems.

The synthesis was carried out by a stepwise elongation method comprising supporting an amino acid corresponding to the C-terminal of oligopeptide to a resin and elongating one amino acid toward the N-terminal, and diisopropylcarbodiimide (DIC) and 1-hydroxybenzotriazole (HOBt) were used as condensing agents in a peptide coupling reaction which corresponds to an elongation reaction. Note that while the amino group of amino acid which was allowed to elongate toward the N terminal was protected by 9-fluorenylmethyloxycarbonyl (Fmoc), amino acids that compose the oligopeptide did not contain side chains with a reaction activity and thus the side chain was not in particular protected.

First, 0.5 g of Fmoc-Pro-Wang resin (0.5 to 0.8 mmol/g, manufactured by Bachem) obtained by protecting the N-terminal of Pro which corresponded to the C-terminal of the oligopeptide, and supporting on a Wang resin through the C-terminal thereof was used. This was put in a reaction vessel of an automatic peptide synthesizer and deprotection of Fmoc was carried out a 20% piperidin-DMF solution for 10 minutes. The resin was washed with DMF for one minute and then Fmoc-Gly-OH, DIC, and HOBt were added 1 mmol each to the reaction solution. The reaction was carried out for one hour. Thereafter, it was made sure that unreacted N termini were not detected and then the resultant was washed with DMF for one minute. Further, deprotection of Fmoc was carried out with 20% piperidin-DMF; the resin was washed with DMF; and then Fmoc-Ala-OH, DIC, and HOBt were added thereto 1 mmol each to allow a reaction. Subsequently, the above procedure was carried out for Pro and Gly by the same method to elongate amino acids one by one. The obtained Fmoc-Gly-Pro-Ala-Gly-Pro-Wang (SEQ ID NO: 23) resin was deprotected with a 20% piperidin-DMF solution for 10 minutes and was dried under reduced pressure. The obtained dried resin was treated with TFA (10 mL×3 times) and an oligopeptide crude product was eluted from the resin into TFA.

The obtained TFA solution was distilled under reduced pressure at room temperature and then diethyl ether 10 mL was added to residues while cooling on ice to obtain a precipitate. Further, the precipitate was washed with diethyl ether (10 mL×5 times) and the resulting precipitate was dried under reduced pressure. The weight of the thus obtained crude product was 38.5 mg (yield 29.8%). The obtained crude product was dissolved in purified water and fractionated to purify by reversed phase high pressure liquid chromatography (HPLC). The purity of the obtained purified product was checked by thin layer chromatography (TLC) and HPLC, and the amino acid sequence thereof was determined by Edman method. It was then confirmed by a mass spectrometer (MALDI-TOF) that the intended molecular weight was attained.

The final weight of intended product was 30.7 mg and the yield thereof was 23.8%.

Using the obtained peptide, the DPP-4 inhibition rate and IC50 value thereof were measured. The result is shown in Table 1.

Example 2 to Example 9

Using Fmoc-Arg(Pbf)-Wang resin, Fmoc-Hyp-Wang resin, Fmoc-Ile-Wang resin, Fmoc-Val-Wang resin, Fmoc-Gln-Wang resin, and Fmoc-Pro-Wang resin as the C-terminal amino acid of an oligopeptide and using Fmoc-Gly-OH, Fmoc-Pro-OH, Fmoc-Leu-OH, and Fmoc-Ile-OH as an Fmoc protected amino acid, Gly-Pro-Ala-Gly-Pro-Arg (SEQ ID NO: 3) (Example 2), Gly-Pro-Ala-Gly-Pro-Hyp (SEQ ID NO: 4) (Example 3), Gly-Pro-Ala-Gly-Pro-Ile (SEQ ID NO: 5) (Example 4), Gly-Pro-Leu-Gly-Pro-Val (SEQ ID NO: 6) (Example 5), Gly-Pro-Ile-Gly-Pro-Val (SEQ ID NO: 7) (Example 6), Gly-Pro-Val (Example 7), Gly-Pro-Gln (Example 8), and Gly-Pro-Ala-Gly (SEQ ID NO: 1) (Example 9), all of which are shown in Table 1 were synthesized according to Example 1.

Note that because, unlike in Example 1, the synthesis of the peptide in Example 2 used Arg which contained two amino groups, Fmoc-Arg(Pbf)-Wang resin in which the guanidine group of the Arg side chain was protected with a Pbf group (2,2,4,6,7-pentamethyldihydrobenzofuran-5-sulfonyl group) was used and the Pbf group was removed by TFA at the end.

In the same manner, because Gln which contained an amide group of the side chain was used in the synthesis of the peptide in Example 8, Fmoc-Gln(Trt)-Wang resin in which the amide group in the Gln side chain was protected by a Trt group (trityl group) was used and the Trt group was removed by TFA at the end.

Using the obtained peptide, the DPP-4 inhibition rate was measured in the same manner as in Example 1. The result is shown in Table 1. In addition, the DPP-4 inhibition curve of the peptide synthesized in Example 6 (Gly-Pro-Ile-Gly-Pro-Val) (SEQ ID NO: 7) was 10 prepared. This inhibition curve is shown in FIG. 1.

Example 10 to Example 15

Using amino acids whose amino group was protected by the Fmoc group, peptides in Examples 10 to 15, the peptides being shown in Table 1, were synthesized in accordance with Example 1 and the DPP-4 inhibition curve was prepared. The result is shown in Table 1. Note that because, unlike in Example 1, the synthesis of the peptide in Example 10 used Glu which contained two carboxyl groups, Fmoc-Glu(OBu$^t$)-Wang resin in which the carboxyl group of the Glu side chain was protected by a tertiary-butyl group (Bu$^t$ group) was used and the Bu$^t$ group was removed by TFA at the end.

Further, as for the peptide in Example 13, using Fmoc-Ser(But)-Wang resin as the C-terminal amino acid of oligopeptide, Gly-Ala-Ile-Gly-Pro-Ser (SEQ ID NO: 9) was synthesized according to Example 1. Note that because, unlike in Example 1, serine which contained a hydroxyl group was used, Fmoc-Ser(But)-Wang resin in which the hydroxyl group of the Ser side chain was protected by a tertiary-butyl group (But group) was used and the But group was removed by TFA at the end.

Comparative Example 1 to Comparative Example 3

Using an amino acid whose amino group was protected by the Fmoc group, peptides in Comparative Example 1 to Comparative Example 3, the peptides being shown in Table 1, were synthesized according to Example 1. Using the obtained peptide, the DPP-4 inhibition rate and $IC_{50}$ value were measured. The result is shown in Table 1. Note that all of the peptides in Comparative Example 1 to Comparative Example 3 were peptides that compose a part of the amino acid sequence of SEQ ID NO: 14.

Note that, in the present application, one that satisfied either a DPP-4 inhibition rate of 30% or less or an $IC_{50}$ of 10 μmol/ml or more was used as the Comparative Example, wherein the DPP-4 inhibition rate and $IC_{50}$ were based on the above method of measurement.

TABLE 1

|  |  | SEQ ID NO: | Molecular weight | Inhibition rate (%) at 0.35 mg/ml time | IC$_{50}$ value (µmol/ml) |
|---|---|---|---|---|---|
| Example 9 | Gly-Pro-Ala-Gly | 1 | 299.3 | Not measured | 0.15 |
| Example 1 | Gly-Pro-Ala-Gly-Pro | 2 | 397.5 | 95.8 | 0.06 |
| Example 2 | Gly-Pro-Ala-Gly-Pro-Arg | 3 | 552.6 | Not measured | 0.08 |
| Example 3 | Gly-Pro-Ala-Gly-Pro-Hyp | 4 | 509.5 | Not measured | 0.07 |
| Example 4 | Gly-Pro-Ala-Gly-Pro-Ile | 5 | 509.6 | Not measured | 0.05 |
| Example 5 | Gly-Pro-Ala-Gly-Pro-Val | 6 | 538.7 | Not measured | 0.024 |
| Example 6 | Gly-Pro-Ala-Gly-Pro-Val | 7 | 538.7 | Not measured | 0.0093 |
| Example 7 | Gly-Pro-Val |  | 271.3 | 76.5 | 0.37 |
| Example 8 | Gly-Pro-Gln |  | 300.3 | 80.2 | 0.31 |
| Example 10 | Gly-Pro-Glu |  | 301.3 | 86.4 | 0.194 |
| Example 11 | Gly-Ala |  | 146.15 | 42.5 | 3.34 |
| Example 12 | Gly-Ala-Ile-Gly-Pro-Ala | 8 | 486.6 | 71.5 | 0.285 |
| Example 13 | Gly-Ala-Ile-Gly-Pro-Ser | 9 | 500.6 | 70.4 | 0.314 |
| Example 14 | Gly-Ala-Val-Gly-Pro-Ala | 10 | 470.5 | 63.7 | 0.437 |
| Example 15 | Gly-Ala-Val-Gly-Pro | 11 | 399.4 | 40.9 | 1.204 |
| Comparative Example 1 | Gly-Pro-Hyp |  | 285.3 | 0 | No inhibitory activity |
| Comparative Example 2 | Gly-Ala-Hyp |  | 259.3 | 0 | No inhibitory activity |
| Comparative Example 3 | Gly-Pro-Pro |  | 382.32 | 10.2 | 78.17 |

(Results)

As shown in Examples 1 to 6, 9, and 12 to 15 in Table 1, when peptides with 4 to 6 amino acids having Gly at the N-terminal and Pro or Ala as the second amino acid residue from the N-terminal had Gly as the fourth amino acid residue from the N-terminal, all had an excellent DPP-4 inhibitory activity regardless of the type of the third amino acid from the N-terminal. In particular, as shown in Examples 1 to 4 and Example 9, the DPP-4 inhibitory activity increased in the peptides having the sequence of Gly-Pro-Ala-Gly (SEQ ID NO: 1) as the length of peptide became longer.

As was clarified when comparing Comparative Example 1 to Comparative Example 3 with Example 7, 8, 10, and 11 in Table 1, in the case of dipeptides or tripeptides, even when the second residue from the N-terminal is Pro or Ala but the third residue therefrom is Hyp, the DPP-4 inhibitory activity was extremely low or the DPP-4 inhibitory activity was not present.

Example 16 to Example 25

Figure 2:
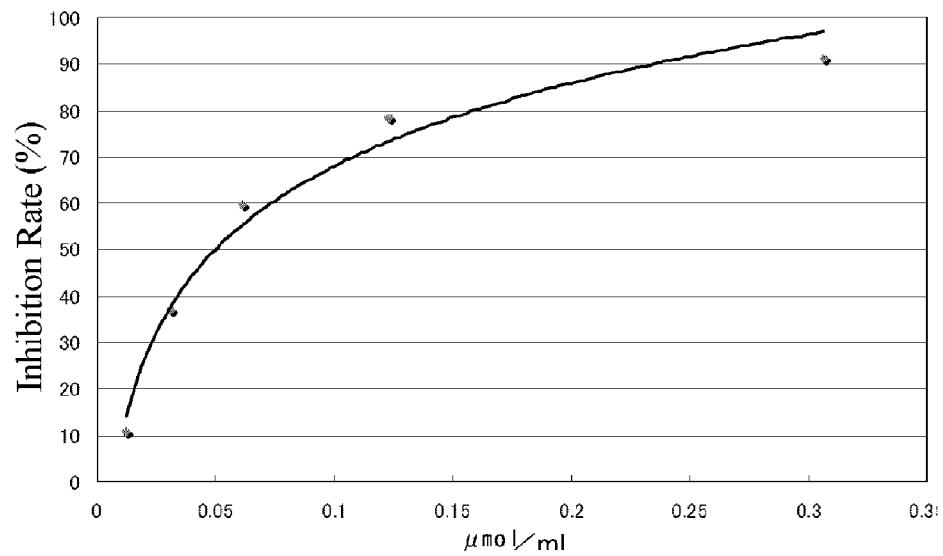
FIG. 2 is a figure showing the DPP-4 inhibition curve of the peptide synthesized in Example 17 (Leu-Pro-Gly)

Using amino acids whose amino group was protected by the Fmoc group, peptides shown in Table 2 were synthesized according to Example 1. In addition, the DPP-4 inhibition curve of the peptide synthesized in Example 17 (Leu-Pro-Gly) was prepared. This inhibition curve is shown in FIG. 2.

Comparative Example 4 to Comparative Example 7

Using amino acids whose amino group was protected by the Fmoc group, peptides in Comparative Example 4 to Comparative Example 7, the peptides being shown in Table 2, were synthesized according to Example 1. Using the obtained peptide, the DPP-4 inhibition rate and IC$_{50}$ value were measured. The result is shown in Table 2. Note that all of the peptides in Comparative Example 4 to Comparative Example 7 were peptides that compose a part of the amino acid sequence of SEQ ID NO: 14.

TABLE 2

|  |  | SEQ ID NO: | Molecular Weight | Inhibition rate (%) at 0.35 mg/ml time | IC$_{50}$ value (µmol/ml) |
|---|---|---|---|---|---|
| Example 16 | Leu-Pro |  | 228.3 | 92.1 | 0.11 |
| Example 17 | Leu-Pro-Gly |  | 285.3 | Not measured | 0.05 |
| Example 18 | Leu-Pro-Gly-Pro-Ala | 12 | 453.5 | 94.9 | 0.063 |
| Example 19 | Ala-Pro-Gly |  | 243.3 | 98.7 | 0.03 |
| Example 20 | Leu-Hyp |  | 244.3 | 48.6 | 1.32 |
| Example 21 | Leu-Hyp-Gly |  | 301.4 | 89.3 | 0.13 |
| Example 22 | Ile-Hyp-Gly |  | 301.4 | 71.0 | 0.50 |
| Example 23 | Leu-Hyp-Gly-Pro-Ala | 13 | 469.5 | 52.1 | 0.83 |
| Example 24 | Pro-Hyp-Gly |  | 285.3 | 27.2 | 4.64 |

TABLE 2-continued

| | SEQ ID NO: | Molecular Weight | Inhibition rate (%) at 0.35 mg/ml time | IC$_{50}$ value (μmol/ml) |
|---|---|---|---|---|
| Example 25 | Ala-Hyp-Gly | 259.3 | 14.6 | 9.45 |
| Comparative Example 4 | Phe-Hyp | 278.3 | 0 | No inhibitory activity |
| Comparative Example 5 | Pro-Hyp | 228.3 | 0 | No inhibitory activity |
| Comparative Example 6 | Ala-Hyp | 202.2 | 0 | No inhibitory activity |
| Comparative Example 7 | Hyp-Gly | 188.2 | 0 | No inhibitory activity |

(Results)

From Example 16 to Example 25 in Table 2, it was found that the DPP-4 inhibitory activity was brought out even when the second amino acid residue from the N-terminal was Hyp. Meanwhile, as was apparent from a comparison of Example 20 with Comparative Examples 4 to 7, the dipeptide with Pro or Hyp as the second amino acid residue from the N-terminal exhibited a tendency that the DPP-4 inhibitory activity greatly varied in the type of amino acid residue at the N-terminal and, in the cases of Phe or Pro, there was no DPP-4 inhibitory activity at all.

Upon comparing Example 25 with Comparative Example 6, when Gly is linked to the dipeptide of Ala-Hyp as the third amino acid residue from the N-terminal, the DPP-4 inhibitory activity is brought out. This tendency was, as shown in Example 21 to Example 25, observed without being limited by the amino acid residue at the N-terminal. Further, as shown in Example 16 to Example 18, observed were tendencies that, also in cases where the second amino acid residue from the N-terminal was Pro, the linkage of Gly at the third position resulted in increased DPP-4 inhibitory activity; and the DPP-4 inhibitory activity was further enhanced as the length of peptide became longer.

The present disclosure is based on Japanese Patent Application No. 2011-242050 filed on Nov. 4, 2011. The description, claims, and drawings of Japanese Patent Application No. 2011-242050 are incorporated into the present specification by reference in their entirety.

INDUSTRIAL APPLICABILITY

According to the present disclosure, a DPP-4 inhibitor derived from collagen that is excellent in safety can be prepared, which is useful.

SEQUENCE LISTING

12F072_ST25.txt

The invention claimed is:

1. A DPP-4 inhibitor comprising a collagen-derived peptide consisting of any one selected from the group consisting of Gly-Pro-Ala-Gly-Pro-Hyp (SEQ ID NO: 4), Gly-Pro-Ala-Gly-Pro-Ile (SEQ ID NO: 5), Gly-Pro-Leu-Gly-Pro-Val (SEQ ID NO: 6) and Gly-Pro-Ile-Gly-Pro-Val (SEQ ID NO: 7) or a mixture of one or more of said peptides or a medically acceptable salt of said peptide or one or more of said peptides as an active ingredient.

2. A composition suitable for oral administration or injection to a human, comprising:
an effective DPP-4 inhibiting amount of the collagen-derived peptide of claim 1 or a mixture of one or more of said peptides or a medically acceptable salt of said peptide or one or more of said peptides; and
a pharmaceutically acceptable carrier suitable for oral or injection administration.

3. The composition of claim 2, wherein the peptide is Gly-Pro-Ala-Gly-Pro-Hyp (SEQ ID NO: 4) or a medically acceptable salt of said peptide.

4. The composition of claim 2, wherein the peptide is Gly-Pro-Ala-Gly-Pro-Ile (SEQ ID NO: 5) or a medically acceptable salt of said peptide.

5. The composition of claim 2, wherein the peptide is Gly-Pro-Leu-Gly-Pro-Val (SEQ ID NO: 6) or a medically acceptable salt of said peptide.

6. The composition of claim 2, wherein the peptide is Gly-Pro-Ile-Gly-Pro-Val (SEQ ID NO: 7) or a medically acceptable salt of said peptide.

7. A composition comprising the collagen-derived peptide of claim 1 or a mixture of said peptides or a medically acceptable salt of said peptide or one or more of said peptides, wherein a dosage is in the form of a tablet, granules, pill, troche or capsule.

8. A food product comprising the collagen-derived peptide of claim 1 or a mixture of said peptides or a medically acceptable salt of said peptide or one or more of said peptides, wherein the food product is selected from the group consisting of beverages, semisolid food products and solid food products.

9. The composition of claim 2, which is suitable for oral administration.

10. The composition of claim 2, which is suitable for injection.

11. The composition of claim 9, wherein a dose comprises 0.001 to 100 mg/kg of peptides or salt thereof.

12. The composition of claim 9, wherein a dose comprises 0.01 to 50 mg/kg of peptides or salt thereof.

13. The composition of claim 9, wherein a dose comprises 0.1 to 10 mg/kg of peptides or salt thereof.

* * * * *

```
                        SEQUENCE LISTING

<160> NUMBER OF SEQ ID NOS: 23

<210> SEQ ID NO 1
<211> LENGTH: 4
<212> TYPE: PRT
<213> ORGANISM: Bos taurus

<400> SEQUENCE: 1

Gly Pro Ala Gly
1

<210> SEQ ID NO 2
<211> LENGTH: 5
<212> TYPE: PRT
<213> ORGANISM: Bos taurus

<400> SEQUENCE: 2

Gly Pro Ala Gly Pro
1               5

<210> SEQ ID NO 3
<211> LENGTH: 6
<212> TYPE: PRT
<213> ORGANISM: Bos taurus

<400> SEQUENCE: 3

Gly Pro Ala Gly Pro Arg
1               5

<210> SEQ ID NO 4
```

```
<211> LENGTH: 6
<212> TYPE: PRT
<213> ORGANISM: Bos taurus
<220> FEATURE:
<221> NAME/KEY: MOD_RES
<222> LOCATION: (6)..(6)
<223> OTHER INFORMATION: Hydrocylation.The Xaa stands for 3Hyp or 4Hyp.

<400> SEQUENCE: 4

Gly Pro Ala Gly Pro Xaa
1               5

<210> SEQ ID NO 5
<211> LENGTH: 6
<212> TYPE: PRT
<213> ORGANISM: Bos taurus

<400> SEQUENCE: 5

Gly Pro Ala Gly Pro Ile
1               5

<210> SEQ ID NO 6
<211> LENGTH: 6
<212> TYPE: PRT
<213> ORGANISM: Artificial Sequence
<220> FEATURE:
<223> OTHER INFORMATION: Modified Collagen Peptide from Bos Taurus
<220> FEATURE:
<221> NAME/KEY: MUTAGEN
<222> LOCATION: (3)..(3)
<223> OTHER INFORMATION: Modified from Ile

<400> SEQUENCE: 6

Gly Pro Leu Gly Pro Val
1               5

<210> SEQ ID NO 7
<211> LENGTH: 6
<212> TYPE: PRT
<213> ORGANISM: Bos taurus

<400> SEQUENCE: 7

Gly Pro Ile Gly Pro Val
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MUTAGEN
<222> LOCATION: (6)..(6)
<223> OTHER INFORMATION: Modified from Ser

<400> SEQUENCE: 8

Gly Ala Ile Gly Pro Ala
1               5

<210> SEQ ID NO 9
<211> LENGTH: 6
<212> TYPE: PRT
<213> ORGANISM: Bos taurus

<400> SEQUENCE: 9

Gly Ala Ile Gly Pro Ser
1               5
```

<210> SEQ ID NO 10
<211> LENGTH: 6
<212> TYPE: PRT
<213> ORGANISM: Bos taurus

<400> SEQUENCE: 10

Gly Ala Val Gly Pro Ala
1               5

<210> SEQ ID NO 11
<211> LENGTH: 5
<212> TYPE: PRT
<213> ORGANISM: Bos taurus

<400> SEQUENCE: 11

Gly Ala Val Gly Pro
1               5

<210> SEQ ID NO 12
<211> LENGTH: 5
<212> TYPE: PRT
<213> ORGANISM: Bos taurus

<400> SEQUENCE: 12

Leu Pro Gly Pro Ala
1               5

<210> SEQ ID NO 13
<211> LENGTH: 5
<212> TYPE: PRT
<213> ORGANISM: Bos taurus
<220> FEATURE:
<221> NAME/KEY: MOD_RES
<222> LOCATION: (2)..(2)
<223> OTHER INFORMATION: Hydroxylation. The Xaa stands for 3Hyp or
      4Hyp.

<400> SEQUENCE: 13

Leu Xaa Gly Pro Ala
1               5

<210> SEQ ID NO 14
<211> LENGTH: 1463
<212> TYPE: PRT
<213> ORGANISM: Bos taurus

<400> SEQUENCE: 14

Met Phe Ser Phe Val Asp Leu Arg Leu Leu Leu Leu Ala Ala Thr
1               5                   10                  15

Ala Leu Leu Thr His Gly Gln Glu Gly Gln Glu Glu Gly Gln Glu
                20                  25                  30

Glu Asp Ile Pro Pro Val Thr Cys Val Gln Asn Gly Leu Arg Tyr His
            35                  40                  45

Asp Arg Asp Val Trp Lys Pro Val Pro Cys Gln Ile Cys Val Cys Asp
    50                  55                  60

Asn Gly Asn Val Leu Cys Asp Asp Val Ile Cys Asp Glu Leu Lys Asp
65                  70                  75                  80

Cys Pro Asn Ala Lys Val Pro Thr Asp Glu Cys Cys Pro Val Cys Pro
                85                  90                  95

Glu Gly Gln Glu Ser Pro Thr Asp Gln Glu Thr Thr Gly Val Glu Gly
                100                 105                 110

-continued

```
Pro Lys Gly Asp Thr Gly Pro Arg Gly Pro Arg Gly Ala Gly Pro
        115                 120                 125
Pro Gly Arg Asp Gly Ile Pro Gly Gln Pro Gly Leu Pro Gly Pro
        130                 135                 140
Gly Pro Pro Gly Pro Pro Gly Pro Pro Gly Leu Gly Gly Asn Phe Ala
145                 150                 155                 160
Pro Gln Leu Ser Tyr Gly Tyr Asp Glu Lys Ser Thr Gly Ile Ser Val
                165                 170                 175
Pro Gly Pro Met Gly Pro Ser Gly Pro Arg Gly Leu Pro Gly Pro
                180                 185                 190
Gly Ala Pro Gly Pro Gln Gly Phe Gln Gly Pro Pro Gly Glu Pro Gly
        195                 200                 205
Glu Pro Gly Ala Ser Gly Pro Met Gly Pro Arg Gly Pro Pro Gly Pro
210                 215                 220
Pro Gly Lys Asn Gly Asp Asp Gly Glu Ala Gly Lys Pro Gly Arg Pro
225                 230                 235                 240
Gly Glu Arg Gly Pro Pro Gly Pro Gln Gly Ala Arg Gly Leu Pro Gly
                245                 250                 255
Thr Ala Gly Leu Pro Gly Met Lys Gly His Arg Gly Phe Ser Gly Leu
        260                 265                 270
Asp Gly Ala Lys Gly Asp Ala Gly Pro Ala Gly Pro Lys Gly Glu Pro
        275                 280                 285
Gly Ser Pro Gly Glu Asn Gly Ala Pro Gly Gln Met Gly Pro Arg Gly
        290                 295                 300
Leu Pro Gly Glu Arg Gly Arg Pro Gly Ala Pro Gly Pro Ala Gly Ala
305                 310                 315                 320
Arg Gly Asn Asp Gly Ala Thr Gly Ala Ala Gly Pro Pro Gly Pro Thr
                325                 330                 335
Gly Pro Ala Gly Pro Pro Gly Phe Pro Gly Ala Val Gly Ala Lys Gly
        340                 345                 350
Glu Gly Gly Pro Gln Gly Pro Arg Gly Ser Glu Gly Pro Gln Gly Val
        355                 360                 365
Arg Gly Glu Pro Gly Pro Pro Gly Pro Ala Gly Ala Ala Gly Pro Ala
        370                 375                 380
Gly Asn Pro Gly Ala Asp Gly Gln Pro Gly Ala Lys Gly Ala Asn Gly
385                 390                 395                 400
Ala Pro Gly Ile Ala Gly Ala Pro Gly Phe Pro Gly Ala Arg Gly Pro
                405                 410                 415
Ser Gly Pro Gln Gly Pro Ser Gly Pro Pro Gly Pro Lys Gly Asn Ser
                420                 425                 430
Gly Glu Pro Gly Ala Pro Gly Ser Lys Gly Asp Thr Gly Ala Lys Gly
        435                 440                 445
Glu Pro Gly Pro Thr Gly Ile Gln Gly Pro Pro Gly Pro Ala Gly Glu
        450                 455                 460
Glu Gly Lys Arg Gly Ala Arg Gly Glu Pro Gly Pro Ala Gly Leu Pro
465                 470                 475                 480
Gly Pro Pro Gly Glu Arg Gly Gly Pro Gly Ser Arg Gly Phe Pro Gly
                485                 490                 495
Ala Asp Gly Val Ala Gly Pro Lys Gly Pro Ala Gly Glu Arg Gly Ala
                500                 505                 510
Pro Gly Pro Ala Gly Pro Lys Gly Ser Pro Gly Glu Ala Gly Arg Pro
        515                 520                 525
Gly Glu Ala Gly Leu Pro Gly Ala Lys Gly Leu Thr Gly Ser Pro Gly
```

```
            530                 535                 540
Ser Pro Gly Pro Asp Gly Lys Thr Gly Pro Pro Gly Pro Ala Gly Gln
545                 550                 555                 560

Asp Gly Arg Pro Gly Pro Gly Pro Pro Gly Ala Arg Gly Gln Ala
                565                 570                 575

Gly Val Met Gly Phe Pro Gly Pro Lys Gly Ala Ala Gly Glu Pro Gly
            580                 585                 590

Lys Ala Gly Glu Arg Gly Val Pro Gly Pro Pro Gly Ala Val Gly Pro
                595                 600                 605

Ala Gly Lys Asp Gly Glu Ala Gly Ala Gln Gly Pro Pro Gly Pro Ala
            610                 615                 620

Gly Pro Ala Gly Glu Arg Gly Glu Gln Gly Pro Ala Gly Ser Pro Gly
625                 630                 635                 640

Phe Gln Gly Leu Pro Gly Pro Ala Gly Pro Pro Gly Glu Ala Gly Lys
                645                 650                 655

Pro Gly Glu Gln Gly Val Pro Gly Asp Leu Gly Ala Pro Gly Pro Ser
                660                 665                 670

Gly Ala Arg Gly Glu Arg Gly Phe Pro Gly Glu Arg Gly Val Gln Gly
            675                 680                 685

Pro Pro Gly Pro Ala Gly Pro Arg Gly Ala Asn Gly Ala Pro Gly Asn
                690                 695                 700

Asp Gly Ala Lys Gly Asp Ala Gly Ala Pro Gly Ala Pro Gly Ser Gln
705                 710                 715                 720

Gly Ala Pro Gly Leu Gln Gly Met Pro Gly Glu Arg Gly Ala Ala Gly
                725                 730                 735

Leu Pro Gly Pro Lys Gly Asp Arg Gly Asp Ala Gly Pro Lys Gly Ala
                740                 745                 750

Asp Gly Ala Pro Gly Lys Asp Gly Val Arg Gly Leu Thr Gly Pro Ile
                755                 760                 765

Gly Pro Pro Gly Pro Ala Gly Ala Pro Gly Asp Lys Gly Glu Ala Gly
            770                 775                 780

Pro Ser Gly Pro Ala Gly Pro Thr Gly Ala Arg Gly Ala Pro Gly Asp
785                 790                 795                 800

Arg Gly Glu Pro Gly Pro Pro Gly Pro Ala Gly Phe Ala Gly Pro Pro
                805                 810                 815

Gly Ala Asp Gly Gln Pro Gly Ala Lys Gly Glu Pro Gly Asp Ala Gly
                820                 825                 830

Ala Lys Gly Asp Ala Gly Pro Pro Gly Pro Ala Gly Pro Ala Gly Pro
            835                 840                 845

Pro Gly Pro Ile Gly Asn Val Gly Ala Pro Gly Pro Lys Gly Ala Arg
850                 855                 860

Gly Ser Ala Gly Pro Pro Gly Ala Thr Gly Phe Pro Gly Ala Ala Gly
865                 870                 875                 880

Arg Val Gly Pro Pro Gly Pro Ser Gly Asn Ala Gly Pro Pro Gly Pro
                885                 890                 895

Pro Gly Pro Ala Gly Lys Glu Gly Ser Lys Gly Pro Arg Gly Glu Thr
                900                 905                 910

Gly Pro Ala Gly Arg Pro Gly Glu Val Gly Pro Pro Gly Pro Pro Gly
            915                 920                 925

Pro Ala Gly Glu Lys Gly Ala Pro Gly Ala Asp Gly Pro Ala Gly Ala
                930                 935                 940

Pro Gly Thr Pro Gly Pro Gln Gly Ile Ala Gly Gln Arg Gly Val Val
945                 950                 955                 960
```

```
Gly Leu Pro Gly Gln Arg Gly Glu Arg Gly Phe Pro Gly Leu Pro Gly
                965                 970                 975
Pro Ser Gly Glu Pro Gly Lys Gln Gly Pro Ser Gly Ala Ser Gly Glu
            980                 985                 990
Arg Gly Pro Pro Gly Pro Met Gly Pro Pro Gly Leu Ala Gly Pro Pro
        995                 1000                1005
Gly Glu Ser Gly Arg Glu Gly Ala Pro Gly Ala Glu Gly Ser Pro
    1010                1015                1020
Gly Arg Asp Gly Ser Pro Gly Ala Lys Gly Asp Arg Gly Glu Thr
    1025                1030                1035
Gly Pro Ala Gly Pro Pro Gly Ala Pro Gly Ala Pro Gly Ala Pro
    1040                1045                1050
Gly Pro Val Gly Pro Ala Gly Lys Ser Gly Asp Arg Gly Glu Thr
    1055                1060                1065
Gly Pro Ala Gly Pro Ala Gly Pro Ile Gly Pro Val Gly Ala Arg
    1070                1075                1080
Gly Pro Ala Gly Pro Gln Gly Pro Arg Gly Asp Lys Gly Glu Thr
    1085                1090                1095
Gly Glu Gln Gly Asp Arg Gly Ile Lys Gly His Arg Gly Phe Ser
    1100                1105                1110
Gly Leu Gln Gly Pro Pro Gly Pro Pro Gly Ser Pro Gly Glu Gln
    1115                1120                1125
Gly Pro Ser Gly Ala Ser Gly Pro Ala Gly Pro Arg Gly Pro Pro
    1130                1135                1140
Gly Ser Ala Gly Ser Pro Gly Lys Asp Gly Leu Asn Gly Leu Pro
    1145                1150                1155
Gly Pro Ile Gly Pro Pro Gly Pro Arg Gly Arg Thr Gly Asp Ala
    1160                1165                1170
Gly Pro Ala Gly Pro Pro Gly Pro Pro Gly Pro Pro Gly Pro Pro
    1175                1180                1185
Gly Pro Pro Ser Gly Gly Tyr Asp Leu Ser Phe Leu Pro Gln Pro
    1190                1195                1200
Pro Gln Glu Lys Ala His Asp Gly Gly Arg Tyr Tyr Arg Ala Asp
    1205                1210                1215
Asp Ala Asn Val Val Arg Arg Asp Leu Glu Val Asp Thr Thr
    1220                1225                1230
Leu Lys Ser Leu Ser Gln Gln Ile Glu Asn Ile Arg Ser Pro Glu
    1235                1240                1245
Gly Ser Arg Lys Asn Pro Ala Arg Thr Cys Arg Asp Leu Lys Met
    1250                1255                1260
Cys His Ser Asp Trp Lys Ser Gly Glu Tyr Trp Ile Asp Pro Asn
    1265                1270                1275
Gln Gly Cys Asn Leu Asp Ala Ile Lys Val Phe Cys Asn Met Glu
    1280                1285                1290
Thr Gly Glu Thr Cys Val Tyr Pro Thr Gln Pro Ser Val Ala Gln
    1295                1300                1305
Lys Asn Trp Tyr Ile Ser Lys Asn Pro Lys Glu Lys Arg His Val
    1310                1315                1320
Trp Tyr Gly Glu Ser Met Thr Gly Gly Phe Gln Phe Glu Tyr Gly
    1325                1330                1335
Gly Gln Gly Ser Asp Pro Ala Asp Val Ala Ile Gln Leu Thr Phe
    1340                1345                1350
```

```
Leu Arg Leu Met Ser Thr Glu Ala Ser Gln Asn Ile Thr Tyr His
    1355                1360                1365

Cys Lys Asn Ser Val Ala Tyr Met Asp Gln Gln Thr Gly Asn Leu
    1370                1375                1380

Lys Lys Ala Leu Leu Leu Gln Gly Ser Asn Glu Ile Glu Ile Arg
    1385                1390                1395

Ala Glu Gly Asn Ser Arg Phe Thr Tyr Ser Val Thr Tyr Asp Gly
    1400                1405                1410

Cys Thr Ser His Thr Gly Ala Trp Gly Lys Thr Val Ile Glu Tyr
    1415                1420                1425

Lys Thr Thr Lys Thr Ser Arg Leu Pro Ile Ile Asp Val Ala Pro
    1430                1435                1440

Leu Asp Val Gly Ala Pro Asp Gln Glu Phe Gly Phe Asp Val Gly
    1445                1450                1455

Pro Ala Cys Phe Leu
    1460

<210> SEQ ID NO 15
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa is Pro or Leu
<220> FEATURE:
<221> NAME/KEY: misc_feature
<222> LOCATION: (3)..(15)
<223> OTHER INFORMATION: Xaa is any amino acid, except Gly
<220> FEATURE:
<221> NAME/KEY: misc_feature
<222> LOCATION: (4)..(15)
<223> OTHER INFORMATION: "Gly Xaa Xaa" may or may not be present

<400> SEQUENCE: 15

Gly Xaa Xaa Gly Xaa Xaa Gly Xaa Xaa Gly Xaa Xaa Gly Xaa Xaa
1               5                   10                  15

<210> SEQ ID NO 16
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is any amino acid residue with an
      isoelectric point of 5.9 to 6.3
<220> FEATURE:
<221> NAME/KEY: misc_feature
<222> LOCATION: (2)..(2)
<223> OTHER INFORMATION: Xaa is Pro, Ala, or Hyp
<220> FEATURE:
<221> NAME/KEY: misc_feature
<222> LOCATION: (3)..(3)
<223> OTHER INFORMATION: Xaa, if present, is any amino acid residue
      other than Hyp, Pro, and Arg
<220> FEATURE:
<221> NAME/KEY: misc_feature
<222> LOCATION: (4)..(4)
<223> OTHER INFORMATION: Xaa, if present, is Gly or Pro
<220> FEATURE:
<221> NAME/KEY: misc_feature
<222> LOCATION: (5)..(5)
<223> OTHER INFORMATION: Xaa, if present, is Pro or Ala
<220> FEATURE:
```

```
<221> NAME/KEY: misc_feature
<222> LOCATION: (6)..(6)
<223> OTHER INFORMATION: Xaa, if present, is any amino acid

<400> SEQUENCE: 16

Xaa Xaa Xaa Xaa Xaa Xaa
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa is Pro or Ala
<220> FEATURE:
<221> NAME/KEY: misc_feature
<222> LOCATION: (3)..(3)
<223> OTHER INFORMATION: Xaa, if present, is any amino acid residue other
      than Hyp, Pro, and Arg
<220> FEATURE:
<221> NAME/KEY: misc_feature
<222> LOCATION: (4)..(4)
<223> OTHER INFORMATION: Xaa, if present, is Gly
<220> FEATURE:
<221> NAME/KEY: misc_feature
<222> LOCATION: (5)..(5)
<223> OTHER INFORMATION: Xaa, if present, is Pro
<220> FEATURE:
<221> NAME/KEY: misc_feature
<222> LOCATION: (6)..(6)
<223> OTHER INFORMATION: Xaa, if present, is any amino acid

<400> SEQUENCE: 17

Gly Xaa Xaa Xaa Xaa Xaa
1               5

<210> SEQ ID NO 18
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is Leu, Ile or Ala
<220> FEATURE:
<221> NAME/KEY: misc_feature
<222> LOCATION: (2)..(2)
<223> OTHER INFORMATION: Xaa is Hyp or Pro
<220> FEATURE:
<221> NAME/KEY: misc_feature
<222> LOCATION: (3)..(3)
<223> OTHER INFORMATION: Xaa, if present, is any amino acid residue
      other than Hyp, Pro, Ile, or Arg
<220> FEATURE:
<221> NAME/KEY: misc_feature
<222> LOCATION: (4)..(4)
<223> OTHER INFORMATION: Xaa, if present, is Pro
<220> FEATURE:
<221> NAME/KEY: misc_feature
<222> LOCATION: (5)..(5)
<223> OTHER INFORMATION: Xaa, if present, is Ala

<400> SEQUENCE: 18

Xaa Xaa Xaa Xaa
1

<210> SEQ ID NO 19
```

```
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa is any amino acid residue with an
      isoelectric point of 3.0 to 6.2 other than Hyp
<220> FEATURE:
<221> NAME/KEY: misc_feature
<222> LOCATION: (4)..(4)
<223> OTHER INFORMATION: Xaa, if present, is Gly
<220> FEATURE:
<221> NAME/KEY: misc_feature
<222> LOCATION: (5)..(5)
<223> OTHER INFORMATION: Xaa, if present, is Pro
<220> FEATURE:
<221> NAME/KEY: misc_feature
<222> LOCATION: (6)..(6)
<223> OTHER INFORMATION: Xaa, if present, is any amino acid

<400> SEQUENCE: 19

Gly Pro Xaa Xaa Xaa Xaa
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa, if present, is any amino acid residue with
      an isoelectric point of 5.8 to 6.2
<220> FEATURE:
<221> NAME/KEY: misc_feature
<222> LOCATION: (4)..(4)
<223> OTHER INFORMATION: Xaa, if present, is Gly
<220> FEATURE:
<221> NAME/KEY: misc_feature
<222> LOCATION: (5)..(5)
<223> OTHER INFORMATION: Xaa, if present, is Pro
<220> FEATURE:
<221> NAME/KEY: misc_feature
<222> LOCATION: (6)..(6)
<223> OTHER INFORMATION: Xaa, if present, is any amino acid

<400> SEQUENCE: 20

Gly Ala Xaa Xaa Xaa Xaa
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(1)
<223> OTHER INFORMATION: Xaa is Leu or Ile
<220> FEATURE:
<221> NAME/KEY: misc_feature
<222> LOCATION: (2)..(2)
<223> OTHER INFORMATION: Xaa is Hyp
<220> FEATURE:
<221> NAME/KEY: misc_feature
<222> LOCATION: (3)..(3)
<223> OTHER INFORMATION: Xaa, if present, is Gly
<220> FEATURE:
<221> NAME/KEY: misc_feature
```

```
<222> LOCATION: (4)..(4)
<223> OTHER INFORMATION: Xaa, if present, is Pro
<220> FEATURE:
<221> NAME/KEY: misc_feature
<222> LOCATION: (5)..(5)
<223> OTHER INFORMATION: Xaa, if present, is Ala

<400> SEQUENCE: 21

Xaa Xaa Xaa Xaa Xaa
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa, if present, is Gly
<220> FEATURE:
<221> NAME/KEY: misc_feature
<222> LOCATION: (4)..(4)
<223> OTHER INFORMATION: Xaa, if present, is Pro
<220> FEATURE:
<221> NAME/KEY: misc_feature
<222> LOCATION: (5)..(5)
<223> OTHER INFORMATION: Xaa, if present, is Ala

<400> SEQUENCE: 22

Leu Pro Xaa Xaa Xaa
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: Fmoc at 5' end
<220> FEATURE:
<221> NAME/KEY: MOD_RES
<222> LOCATION: (5)..(5)
<223> OTHER INFORMATION: Wang resin at 3' end

<400> SEQUENCE: 23

Gly Pro Ala Gly Pro
1               5
```